US00PP32445P2

(12) United States Plant Patent
Moucheboeuf

(10) Patent No.: US PP32,445 P2
(45) Date of Patent: Nov. 10, 2020

(54) ***DIANTHUS* PLANT NAMED 'WP19 PIE65'**

(50) Latin Name: ***Dianthus allwoodii* hort.**
Varietal Denomination: WP19 PIE65

(71) Applicant: Plant Genetics International, Ltd., Hambrook (GB)

(72) Inventor: Laetitia Moucheboeuf, Dawlish (GB)

(73) Assignee: Plant Genetics International, Ltd., Hambrook (GB)

( * ) Notice: Subject to any disclaimer, the term of this patent is extended or adjusted under 35 U.S.C. 154(b) by 0 days.

(21) Appl. No.: 16/873,081

(22) Filed: Jan. 29, 2020

(51) Int. Cl.
*A01H 5/02* (2018.01)
*A01H 6/30* (2018.01)

(52) U.S. Cl.
USPC ..... Plt./278
CPC ..... *A01H 6/305* (2018.05)

(58) Field of Classification Search
USPC ..... Plt./278, 283
CPC ..... A01H 5/0233
See application file for complete search history.

*Primary Examiner* — Kent L Bell
(74) *Attorney, Agent, or Firm* — Barbara Campbell; Weatherly IP Solutions, LLC

(57) ABSTRACT

A new cultivar of *Dianthus* plant named 'WP19 PIE65' that is characterized by a compact mounding habit, large single bright crimson flowers, blooming from May through October, with a medium, clove-like fragrance, glaucous blue green foliage, suitable for use as a flowering plant in pots and containers as well as for use as a cut flower and in bouquets, is disclosed.

2 Drawing Sheets

Genus and species: *Dianthus allwoodii* hort.
Variety denomination: 'WP19 PIE65'.

BACKGROUND OF THE NEW PLANT

The present invention relates to a new and distinct cultivar of hardy *Dianthus*, commonly known as Garden Pink, which is grown for use as a flowering plant for pots and containers and for planting in the garden and landscape. The new cultivar is known botanically as *Dianthus allwoodii* hort. and will be referred to hereinafter by the cultivar name 'WP19 PIE65'.

'WP19 PIE65' is a complex hybrid plant that is the product of a long-term breeding program conducted in a cultivated area of Ashcombe Road, Dawlish, Devon, United Kingdom. 'WP19 PIE65' was selected in 2016 for its large single vibrant crimson flowers, medium clove-like fragrance and glaucous blue-green foliage.

'WP19 PIE65' arose and was selected as a seedling which resulted from the controlled pollination of two prior selections of *Dianthus*. The male parent is *Dianthus* code name 'GI14415' (unpatented and unreleased) and the female parent is *Dianthus* code name 'GI116' (unpatented and unreleased). The male parent and female parent had both been grown within the inventor's stock of breeding lines.

Asexual reproduction of 'WP19 PIE65' was first accomplished in 2016 in a cultivated area of Ashcombe, United Kingdom using the propagation method of shoot cuttings. 'WP19 PIE65' has been determined to be stable and reproduces true to type in successive generations of asexual propagation.

SUMMARY

The following traits have been repeatedly observed and represent the characteristics of the new *Dianthus* cultivar 'WP19 PIE65'. 'WP19 PIE65' has not been tested under all possible conditions and phenotypic differences may be observed with variations in environmental, climatic and cultural conditions, however, without any variance in genotype.

1. 'WP19 PIE65' exhibits a compact mounding habit.
2. 'WP19 PIE65' bears large single vibrant crimson flowers.
3. The petals of 'WP19 PIE65' are flat.
4. 'WP19 PIE65' blooms from May through October.
5. The flowers of 'WP19 PIE65' exhibit a medium, clove-like fragrance.
6. 'WP19 PIE65' exhibits glaucous blue green foliage.
7. At maturity, the height of the foliage mound of 'WP19 PIE65' is 40 cm, and the width is 30 cm to 35 cm.
8. 'WP19 PIE65' is perennial and is hardy at least to minus 15° Centigrade.
9. 'WP19 PIE65' is suitable for use as a flowering plant in pots and containers, and for use as a cut flower and in bouquets.

BRIEF DESCRIPTION OF THE PHOTOGRAPHS

The accompanying color photographs illustrate the overall appearance of the new *Dianthus* variety 'WP19 PIE65' showing colors as true as it is reasonably possible to obtain in colored reproductions of this type. Colors in the photographs may differ from the color values cited in the detailed botanical description, which accurately describe the actual colors of the new variety 'WP19 PIE65'.

Figure 1:
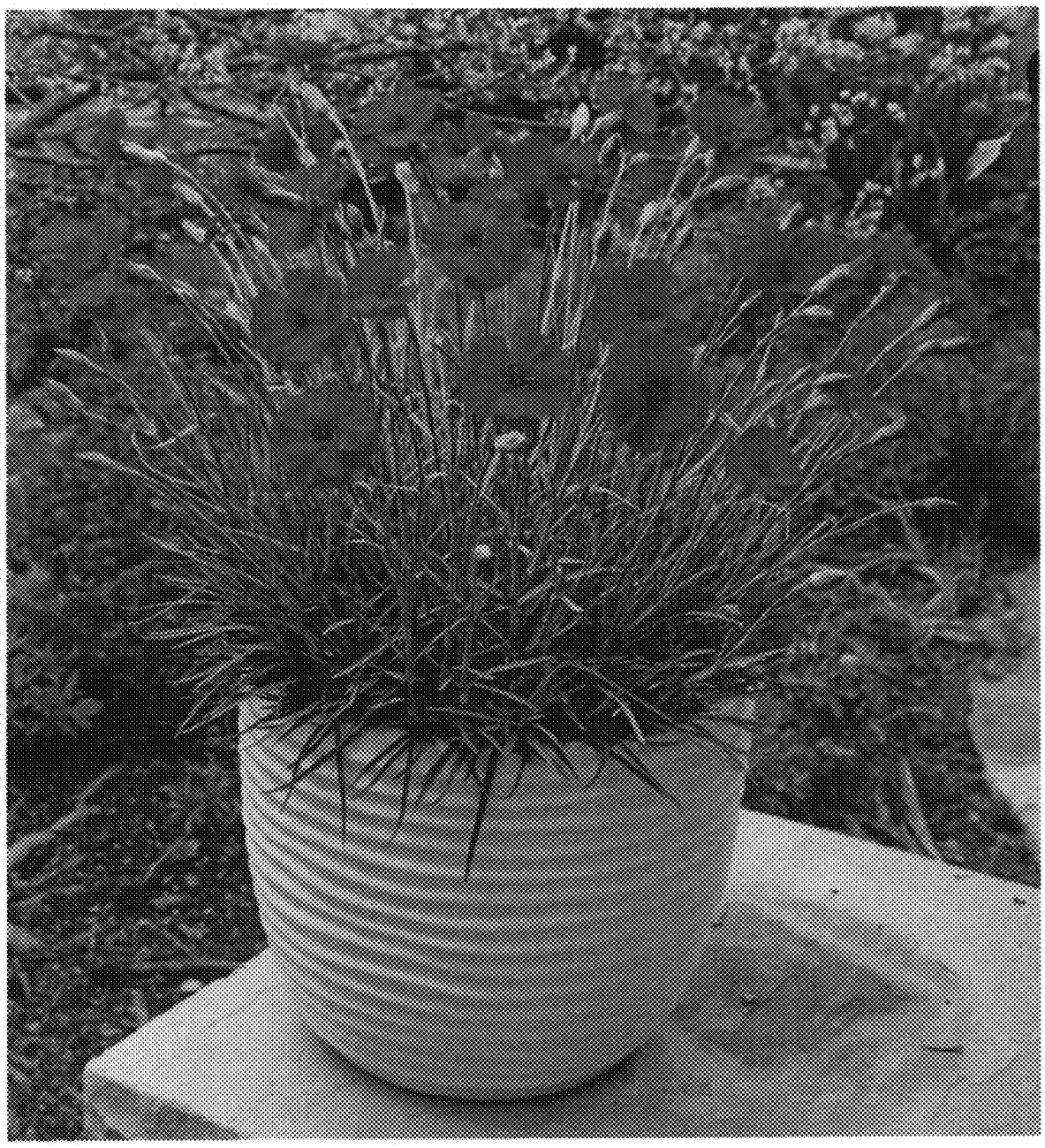
FIG. 1 depicts an entire flowering plant of 'WP19 PIE65'.
Figure 2:
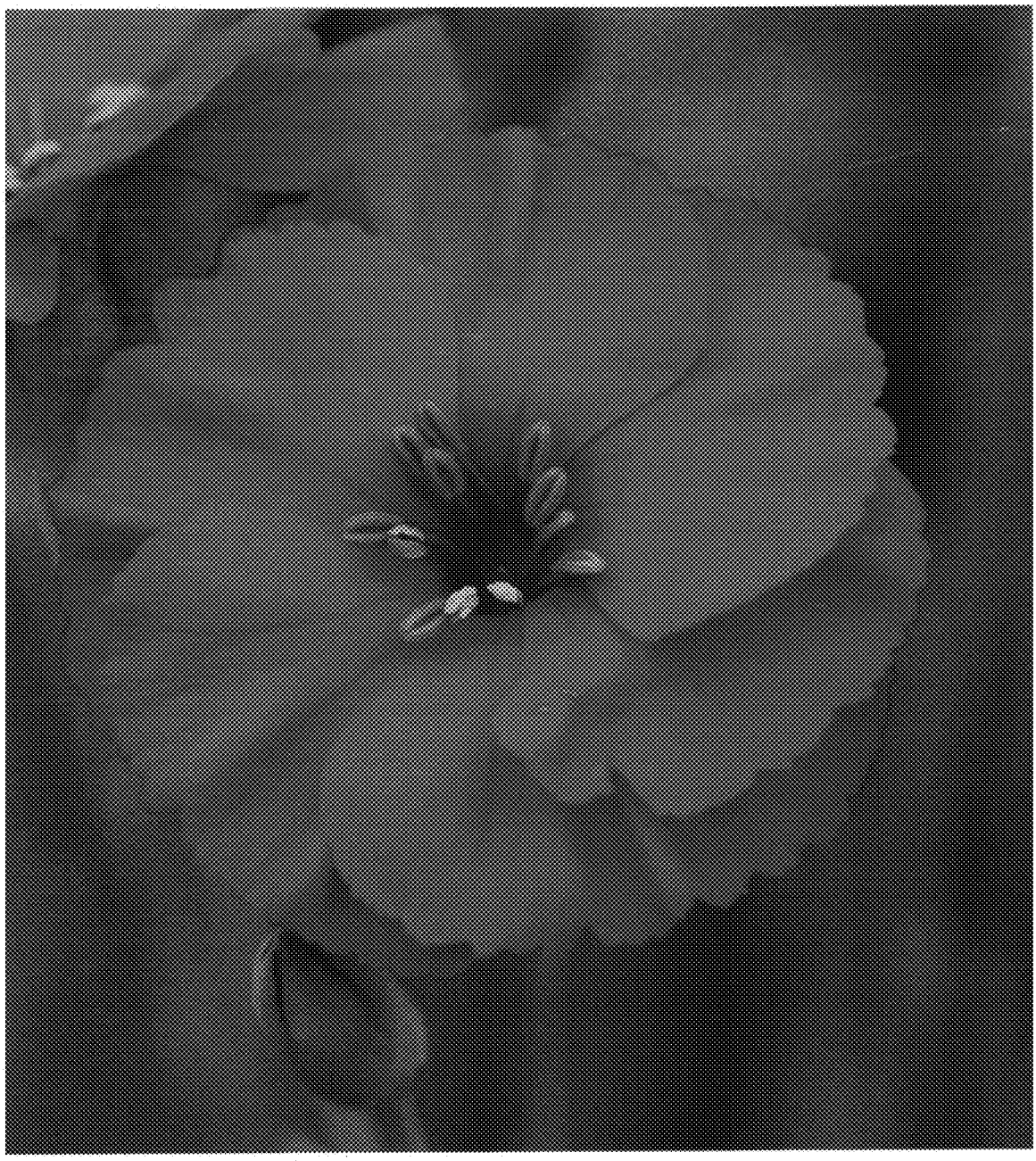
FIG. 2 depicts a close-up view of the flower of 'WP19 PIE65'.

The photograph in FIG. 1 was taken in May 2019 from a plant which had been grown outdoors in a 2-gallon container in Oxnard, Calif. The photograph in FIG. 2 was taken in May 2018 from a plant which was growing in the inventor's greenhouse in Devon, United Kingdom. No chemicals were used to treat the plants. All photographs were made using conventional techniques and although colors may appear different from actual colors due to light reflectance, they are as accurate as possible by conventional photography.

BOTANICAL DESCRIPTION OF THE PLANT

The following is a detailed description of the new cultivar 'WP19 PIE65'. Data was collected from plants grown in 3-liter containers under an unheated glasshouse in Ashcombe, Dawlish, United Kingdom. The color determinations are in accordance with the sixth edition (2015) of The Royal Horticultural Society Colour Chart of The Royal Horticultural Society, London, England, except where general color terms of ordinary dictionary significance are used. No chemicals were used to treat the plants. Growing conditions are typical of *Dianthus*.

Botanical classification: *Dianthus*.

*Variety*.—'WP19 PIE65'.

*Species*.—X *allwoodii*.

*Common names*.—Hybrid *Dianthus*, Garden Pink.

*Commercial classification*.—Hardy perennial.

*Use*.—Ornamental plant for pots and containers.

Parentage: 'WP19 PIE65' is a hybrid plant that resulted from the controlled cross-pollination between two *Dianthus* x *allwoodii* plants.

*Female parent plant*.—'GI116' experimental *Dianthus* plant (unpatented).

*Male parent plant*.—'GI14415' experimental *Dianthus* plant (unpatented).

Plant description:

*Bloom period*.—May to October.

*Plant habit*.—Compact mounding habit.

*Plant height*.—40 cm in overall height, including flower canopy.

*Plant width*.—30 cm to 35 cm in width.

*Plant hardiness*.—Hardy to minus 15° Centigrade.

*Type*.—Perennial.

*Root system*.—Fibrous.

*Propagation*.—Propagation is accomplished using shoot cuttings.

*Cultural requirements*.—Plant in full sun, well-drained and moderately fertile soil and keep well fertilized and watered.

*Time required to produce a rooted cutting*.—5 weeks are needed to produce a rooted cutting.

*Temperature recommended for cuttings to produce roots*.—The air temperature needed is a minimum of 15° Centigrade air temperature and base heat of 21° Centigrade.

*Crop time*.—6 to 9 months is needed to produce a finished 3-litre container size from a well-rooted cutting.

Stem:

*Shape*.—Cylindrical, solid.

*Dimensions*.—13 cm in length, 4 mm to 5 mm diameter.

*Surface*.—Glabrous and glaucous.

*Color*.—RHS 145B, RHS 145C and RHS 145D (in the sheathing zone).

*Branching*.—Numerous shoots from the axils of the lower leaves.

*Internode length*.—4 mm to 6 mm between nodes (before extension of peduncle).

*Node dimensions*.—4 mm in diameter and 5 mm in length.

Leaf:

*Type*.—Evergreen.

*Dimensions*.—8 to 9 cm in length, 3 mm in width.

*Color adaxial surface*.—RHS N189C

*Color abaxial surface*.—RHS 189A

*Shape*.—Linear.

*Division*.—Simple.

*Apex*.—Acute.

*Base*.—Decurrent.

*Venation*.—Absent on the adaxial surface and only one central vein visible on the abaxial surface. Vein color RHS 189A.

*Margins*.—Entire.

*Attachment*.—Sheathing.

*Arrangement*.—Opposite and spiraling up stem.

*Surfaces* (*adaxial and abaxial*).—Glaucous.

*Fragrance*.—Absent.

Flowers:

*Inflorescence*.—Simple cyme.

*Type*.—Single, polypetalous.

*Number*.—3 to 5 per stem.

*Dimensions* (*including calyx*).—41 mm in length and 53 mm in diameter.

*Shape*.—Circular.

*Lastingness*.—10 days at 20° Celsius on the plant; 8 to 10 days off the plant.

*Fragrance*.—Medium, clove-like.

*Flowering period*.—May to October.

Peduncle:

*Shape*.—Cylindrical, solid.

*Dimensions*.—34 cm to 38 cm in length, 3 mm in diameter.

*Surface*.—Glabrous, waxy.

*Strength*.—Strong, rigid.

*Color*.—RHS 122A.

Bud:

*Shape*.—Oblong.

*Color*.—RHS N138A to RHS N138B on apical half and RHS 144B to RHS 144C on basal half (below the bracts).

*Anthocyanin*.—Present, as a very thin line along the edge of the lobes, color RHS 61B.

*Dimensions*.—28 mm in length and 9 mm in width.

Petals:

*Petal arrangement*.—Persistent, apopetalous and overlapping.

*Petal shape*.—Corolla flat, blade slightly waved, flat in profile.

*Margin*.—Crenate-dentate.

*Indentations*.—Up to 1 mm deep.

*Texture*.—Soft.

*Type*.—Single.

*Number of petals*.—5.

*Dimensions*.—52 mm in length, 36 mm in width.

*Petal shape*.—Fan shape.

*Petal surface*.—Glabrous.

*Petal apex*.—Fan shaped, crenate-dentate.

*Petal base*.—Strap shaped, tapering towards base.

*Color pattern*.—Blade is vibrant crimson, with a small dark crimson band.

*Petal color* (*adaxial surface*).—Ground color of blade: brighter and redder than RHS 53A. Color of band:

RHS 46A. Color of middle of strap: RHS 145C. Color of base of strap: RHS 145D.

*Petal color* (*abaxial surface*).—Ground color of blade: RHS 59A. Color of middle of strap: RHS 145C. Color of base of strap: RHS 145D.

Calyx:

*Dimensions*.—24 mm in length and 10 mm in width.

*Shape*.—Cylindrical and straight.

*Sepals*.—5, fused up to 7 mm below the apex.

*Sepal dimensions*.—28 mm in length and 5 mm in width.

*Apex*.—Acute.

*Base*.—Truncate.

*Color of sepals, outer surface*.—RHS N138A to RHS N138B on apical half and RHS 144B to RHS 144C on basal half (below the bracts).

*Color of sepals, inner surface*.—RHS 139D.

*Anthocyanin*.—Present, as a very thin line along the margin of the lobes, color 61B; and sometimes appearing as pink blush on the calyx itself.

*Splitting*.—Not observed.

Epicalyx:

*Number of bracts*.—1 pair of 2.

*Bracts shape*.—Medium acuminate.

*Bracts dimensions*.—9 mm in length and 10 mm in width.

*Bracts color*.—RHS N138A, RHS N138B, RHS N138C and RHS 144B, RHS 144C, RHS 144D are all present.

*Anthocyanin*.—Occasionally present as a blush, color 61B, on the margin of the apex.

*Number of bracteoles*.—1 pair of 2.

*Bracteoles shape*.—Medium acuminate.

*Bracteoles dimensions*.—10 mm in length and 12 mm in width.

*Bracteoles color*.—RHS N138A, RHS N138B, RHS N138C and RHS 144B, RHS 144C, RHS 144D are all present.

*Bracteoles anthocyanin*.—Present as a blush, color 61B, on the edge of the apex, inconsistent and not always present.

Reproductive organs:

*Stamen number*.—10.

*Stamen dimensions*.—30 mm length and 1 mm diameter.

*Color of filaments*.—RHS N155A or whiter at base, becoming deep red 60A towards the anthers.

*Anther number*.—10.

*Anther dimensions*.—4 mm length and 2 mm in diameter.

*Color of anthers*.—RHS 58A (when fresh anthers).

*Anther attachment*.—Dorsifixed.

*Pollen*.—Present, moderate quantity, colors RHS N187D, RHS 202C are all present.

*Style number*.—2 to 3. Where present, third style may be longitudinally fused to one other.

*Style shoulder*.—Absent.

*Color of style*.—RHS N155A or whiter at base, then dark purple-red RHS 59A. Style dimensions (including stigma): 34 mm to 38 mm in length and 1 mm in width.

*Stigma number*.—One on each style.

*Stigma color*.—RHS 59A.

*Stigma dimensions*.—14 to 18 mm long, linear and affixed longitudinally to uppermost section of style, exserted approximately 5 mm above petals at maturity.

*Ovary position*.—Superior.

*Ovary dimensions*.—9 mm in length and 8 mm in diameter.

*Ovary shape*.—Rhombic.

*Ovary surface and texture*.—Smooth and slightly ribbed.

*Ovary color*.—RHS 145B at the uppermost surface, becoming paler RHS 149D and RHS 145D at the lowest surface.

Seed:

*Color*.—RHS 202A.

*Length*.—4 mm.

*Diameter*.—3 mm.

*Shape*.—Oval and flattened.

*Surface*.—Crinkled.

*Number*.—Varies, up to 20 per pod.

Diseases and pests: 'WP19 PIE65' is susceptible to known *Dianthus* pests and diseases.

COMPARISON WITH PARENTAL LINES AND KNOWN VARIETY

'WP19 PIE65' is distinguishable from the male parent as follows. The flower color of 'GI14415' is light to medium magenta with no band. The foliage mound of 'GI14415' is slightly higher with slightly broader leaves than the foliage of 'WP19 PIE65'. Both varieties are of similar flowering height.

'WP19 PIE65' is distinguishable from the female parent as follows. The female parent 'GI116' bears dark pink flowers and is taller overall than 'WP19 PIE65' when both varieties are grown outside.

The variety of *Dianthus* considered to most closely resemble 'WP19 PIE65' is *Dianthus* Plant Named 'WP17 PIE54' (U.S. Plant Pat. No. 30,245). In comparison with 'WP17 PIE54', 'WP19 PIE65' bears single vibrant crimson flowers. Whereas the foliage habit of 'WP19 PIE65' is tight and compact, the foliage habit of 'WP17 PIE54' is loose and more open.

I claim:

1. A new and distinct cultivar of *Dianthus* plant named 'WP19 PIE65' as described and illustrated herein.

* * * * *